United States Patent [19]

Hagner et al.

[11] 4,353,618
[45] Oct. 12, 1982

[54] OPTICAL ARRANGEMENT FOR THE REFLECTING MICROSCOPIC EXAMINATION OF AN OBJECT

[75] Inventors: Willi Hagner, Solms; Andreas Thaer, Leihgestern; Francis Bigar, Zurich, all of Fed. Rep. of Germany

[73] Assignee: Ernst Leitz Wetzlar GmbH, Wetzlar, Fed. Rep. of Germany

[21] Appl. No.: 91,819

[22] Filed: Nov. 6, 1979

[30] Foreign Application Priority Data

Nov. 9, 1978 [DE] Fed. Rep. of Germany ....... 2848590

[51] Int. Cl.³ ............................................. G02B 21/12
[52] U.S. Cl. ........................................ 350/91; 351/16
[58] Field of Search .................. 350/17, 91, 448, 235, 350/237, 276 SL, 286, 287; 356/135, 136; 351/16, 15, 14, 1

[56] References Cited

U.S. PATENT DOCUMENTS 3,746,450  7/1973  Smith .................................. 356/135

FOREIGN PATENT DOCUMENTS 713853  11/1931  France ................................. 350/448
255408  3/1964  Netherlands ........................ 356/136

*Primary Examiner*—Jon W. Henry
*Attorney, Agent, or Firm*—Schwartz, Jeffery, Schwaab, Mack, Blumenthal & Koch

[57] ABSTRACT

An optical system for the reflecting microscopic examination of objects. An illuminating beam path and an observation beam path are provided along with an optical lens such that the beam paths pass through the optical lens and make an angle with each other. The lens is made up of two portions interfacing in a plane which bisects the angle of the beam paths and is perpendicular to a plane containing the beam paths. The interface between the lens portions is at least partially opaque and serves to absorb or reflect light reflected from the lens-/object interface and thereby prevents such light from obscuring light reflected from surfaces interior to the object. The optical system is particularly advantageous for the examination of biological tissue such as the endothelium layer of the cornea of the eye.

7 Claims, 9 Drawing Figures

OPTICAL ARRANGEMENT FOR THE REFLECTING MICROSCOPIC EXAMINATION OF AN OBJECT

BACKGROUND OF THE INVENTION

The present invention concerns in general an optical arrangement for the reflecting microscopic examination of an object, and in particular biological tissues and the interior or rear surfaces of organs such as the endothelium layer of the cornea of the eye.

Numerous materials and especially biological objects must be microscopically examined with incident light because they are inaccessible to back light. When structures of objects underneath the surface of a translucent or transparent material are the subject of examination, incident light reflections from the surface are often superposed on the image of such object structures. The intensity of such surface reflections is, in most cases, significantly stronger than the light reflected or remitted by the object structures to be reproduced, because index of refraction of such object structures usually differs very slightly from that of their environment.

A typical example of a reflecting object structure underneath the surface of an organ is the corneal endothelium of the eye, which is located approximately 0.5 to 0.7 mm below the surface of the cornea. Under the usual vertical incident light illumination, the reflection of light from the corneal surface is superposed for the most part on the image of the endothelium. Similar problems are also encountered during the examination of the rear section of the eye because of additional incident light reflections from the lens of the eye. Therefore, there has been a long felt need to suppress or eliminate such interferring reflections especially in ophthalmological instruments.

It is known that surface reflections affecting observation may be reduced by dividing the cornea of the eye being examined into separate zones for illumination and for observation. This division may be effected either in the close vicinity of the eye under examination or in the vicinity of the eye of the observer.

A prior art arrangement is shown in West German Pat. No. PS 323 161, wherein with the aid of a deflecting prism placed in front of the eye being examined, a slit like diaphragm is reproduced on one half of the pupil of the eye. The beam of light passes through the eye lens and illuminates part of the retina, which is then observed through the half of the pupil not illuminated. An overlap of the two halves of the pupil is prevented by the development of a special system for providing parallel beams for illumination and observation. Because the two beams are parallel to each other in front of the eye being examined, no reflections are able to enter the observation beam path from the surface of the cornea. However, it is not possible to observe the front portions of the eye with such parallel beams.

Similar difficulties are encountered in the arrangement shown in West German Pat. No. P 627 621, wherein the illuminating beam is reflected into the eye by means of a deflecting mirror so that parts of the optical system for observation may also be used for the illuminating beam. Adjacent to the edge of the deflecting mirror located on the optical axis of the system, a separating wall is provided, thus affording an additional separation of the two beam paths.

In West German Pat. No. P 394 227, the illuminating beam is again conducted onto the eye to be examined by means of a specially shaped prism in front of the eye, eccentrically placed with respect to the observation beam path. The observation itself takes place through a narrow slit arranged in the vicinity of the eye to be observed. Here, the direction of observation coincides with the direction of the normal to the surface being examined, so that the illuminating beam regularly reflected from the surface of the cornea cannot enter the path of the observation beam.

Another apparatus for suppressing corneal reflections includes placing a contact lens on the eye to be examined. Such an arrangement, described in West German Offenlegungsschrift OS No. 26 05 786, also serves to observe the inside of the eye. The illuminating light is conducted by means of optical conductors, placed at the rim of the contact lens into the eye. Here, interferring reflected beams from the internal surfaces of the eye are directed primarily in the direction of the optical axis of the contact lens so that observation of an object surface free of reflections is possible outside of said axis. Of course, the illumination of front surfaces of the eye is not possible with this arrangement.

A slit lamp type instrument for eye examinations is shown in West German Pat. PS 814 798, wherein the optical axes of the illumination and observation beam paths are in the plane of a normal to the surface of the eye to be examined. The inclination of the optical axes to the normal to the surface may be varied by rotating the observation and the illuminating system around a common axis. This axis is located in the intersection of the two optical axes and extends through the pupil or the object location to be examined inside the eye. No measures are provided for the elimination of interferring reflections during the examination of front sections of the eye. In investigating the rear area of the eye, a contact lens may be placed on the eye to be examined in order to eliminate the refractive power of the lens of the eye.

The difficulties arising during the observation of the front sections of the eye due to interferring reflections from adjacent surfaces, particularly the surface of the cornea, are described in West German Offenlegungsschrift No. 26 50 650. According to this reference, to eliminate the reflections, either the size of the slit-like luminous field may be restricted, or polarized light may be used. With polarized light, the components of the light ordinarly reflected from the surface of the cornea may be suppressed by means of the arrangement of an analyzer in the path of the observations beam. Both of the methods are inadequate for the observation of surfaces underneath but close to the corneal surface, especially of the endothelium, because the overlap of the interferring reflection and the image of the object is in an inverse proportion to the distance between the object reflecting surface and the corneal surface. Additionally, the depolarizing effect produced within the object layer trans-irradiated by the inhomogeneity of the refractive indices is very slight so that the light components passed by the analyzer are most insufficient for observation. While the visual observation is merely rendered very difficult by the superposition of the object and corneal reflections, it becomes entirely impossible when effected by means of electronic imaging (as in a television camera) because the usual automatic brightness control reacts to the brighter reflection. The image of the object, already weak, is then completely suppressed.

SUMMARY OF THE INVENTION

It is thus the object of the invention to provide an arrangement whereby interferring reflections from the surfaces of organs during the examination of the surfaces or organs or tissues located beneath said reflecting surfaces by means of a reflecting microscope, are suppressed. It is a further object of the present invention to reduce interferring reflections not only in slit lamp instruments using relatively large angles of incidence between the observation and illumination beams, but also in instruments with common front lenses for both illumination and observation.

The above and other objects are attained by providing an optical system for reflecting microscopic examination of an interior surface of an object comprising: an imaging optical means for providing an illuminating beam having a path on a first axis; a viewing means for providing an observation beam having a path along the second axis; lens means for directing the illuminating beam to the object and for directing light reflected from the interior surface of said object being examined along the observation beam path, said first and second axes forming an angle therebetween in the region of said lens means, the lens means comprising: a first lens portion positioned in said illuminating beam path, a second lens portion positioned in said observation beam path, and said first and second lens portions having a light impermeable surface therebetween, said light impermeable surface positioned in a plane bisecting the angle between the first and second axes, whereby said light impermable surface prevents undesirable reflected light from said illuminating beams from entering said observation beam path but permits reflected light from said interior surface to enter said observation beam path to be examined.

The lens means in a preferred embodiment is a common optical element resting on the surface of the object. The optical element comprises two cemented parts with their cemented interface between the optical axes of the illuminating and observation beam paths and perpendicular to the plane defined by the two optical axes and provided at least in part with an opaque coating.

BRIEF DESCRIPTION OF THE DRAWINGS

A more complete appreciation of the invention and the attendant advantages thereof will be more clearly understood by reference to the following drawings, wherein.

DETAILED DESCRIPTION OF PREFERRED EMBODIMENTS

The common optical element may be in various embodiments external to or included as the front lens of the optical devices of the illuminating and observation arrangements. It may, however, also be designed on its side facing the illuminating and the observation optical elements as a pentagonal ridge prism or in the form of a parallel plane plate, so that the magnification and the numerical aperture are not affected. It is of advantage to provide the optical element on its contact side with a cavity for the containment of immersion media having refractive indices adapted to that of the object. The effect of the optical element according to the invention may be enhanced advantageously by the insertion variable aperture diaphragms in the illuminating and/or observation beam paths, which specifically may be operated independently of each other. They may also be provided in the form of sliding diaphragms adumbrating the beam paths unilaterally from the inside.

The optical contact element of the invention makes it possible to effect the geometric separation of the illuminating and the observation beam paths necessary to free the observation process of reflections as closely to the object to be examined as at all feasible. Reflections generated on the surface of the object are suppressed entirely. The insertion of an immersion layer with a refractive index close to that of the object, increases the distance between the front edge of the diaphragm rejecting the reflections in the optical element and the surface of the object to be examined. In this manner, a larger object field may be illuminated. By the insertion of aperture diaphragms the opening of the illuminating cone may be adjusted so that all of the beam reflected by the cemented interface is effectively suppressed in the optical element. Particularly during the observation of objects with a plurality of reflecting layers located behind each other (in the direction of radiation), it is important to be able to restrict the angles of reflection to the extent that no reflected rays may enter the path of the observation beam below or above the cemented surface in the optical element. This is especially important in arrangements with variable illumination and observation angles. It is, however, often sufficient to influence the beams incident in the vicinity of the bisector of the angle between the illuminating and the observation directions only. Herein, a diaphragm trimming the cone of light unilaterially from the inside, is particularly advantageous.

Figure 1:
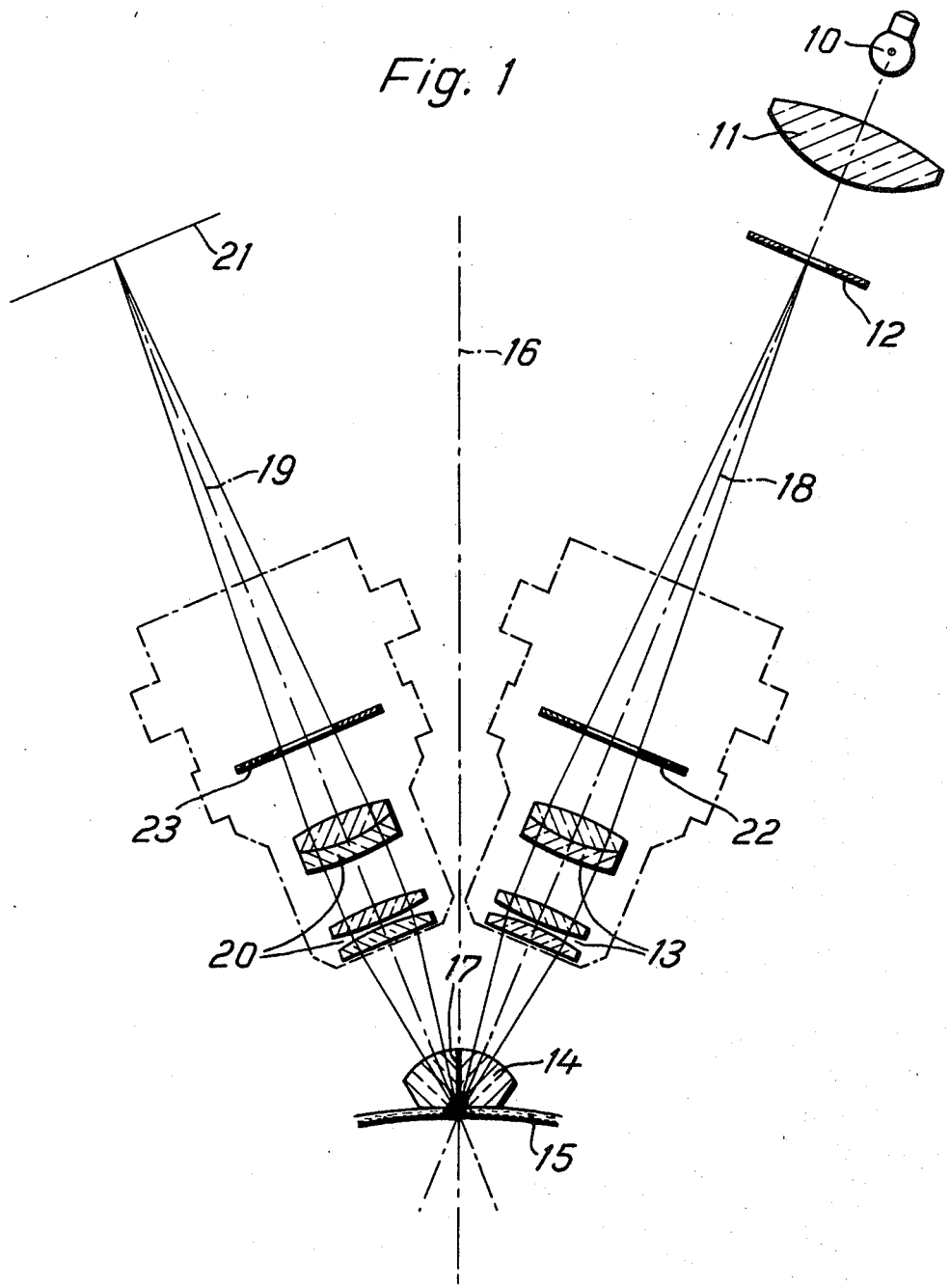
FIG. 1 is a side cross-sectional view showing separate illuminating and observation devices.

Referring now to the drawings wherein like reference characters designate like parts in the several views, FIG. 1 displays on the right half the illuminating beam path and on the left half the observation beam path. In the illuminating beam path, a source of light 10 illuminates, by way of a condenser lens 11, the aperture (preferably a slit-like aperture) of a luminous field diaphragm 12. With the aid of an optical system 13, a reduced image of the luminous field diaphragm is produced on the surface of the object to be examined. An optical element 14 resting in contact on the subject 15 is included in said imaging beam path.

In one embodiment, the optical system 13 is the objective of a microscope. The corneal endothelium of the eye serves as the object of the examination. The optical element 14 is designed in the form of a planoconvex lens with its planar side in contact with the cornea of the eye. A normal 16 to the object passes through a connecting layer 17 connecting two portions of the optical element 14. The connecting layer 17 is provided with a coating impermeable to light and is vertical to the plane of the drawing. The angle of the optical axis 18 of the illuminating beam path to the normal 16 may be varied between approximately 10° and 45°. The optical axis 19 of the observation beam path includes the same angle as the optical axis 18 with the normal 16. An optical system 20, also representing the objective of a microscope, produces in cooperation with the optical element 14 an enlarged image of the object surface being examined in the plane 21. Aperture diaphragms 22 and 23 are located respectively in the rear focal plane of the optical systems 13 and 20 in the respective illuminating and the observation beam paths. The diaphragms limit the illumination or reflection cones going to or coming from individual points of the object, in a known manner.

Figure 2:
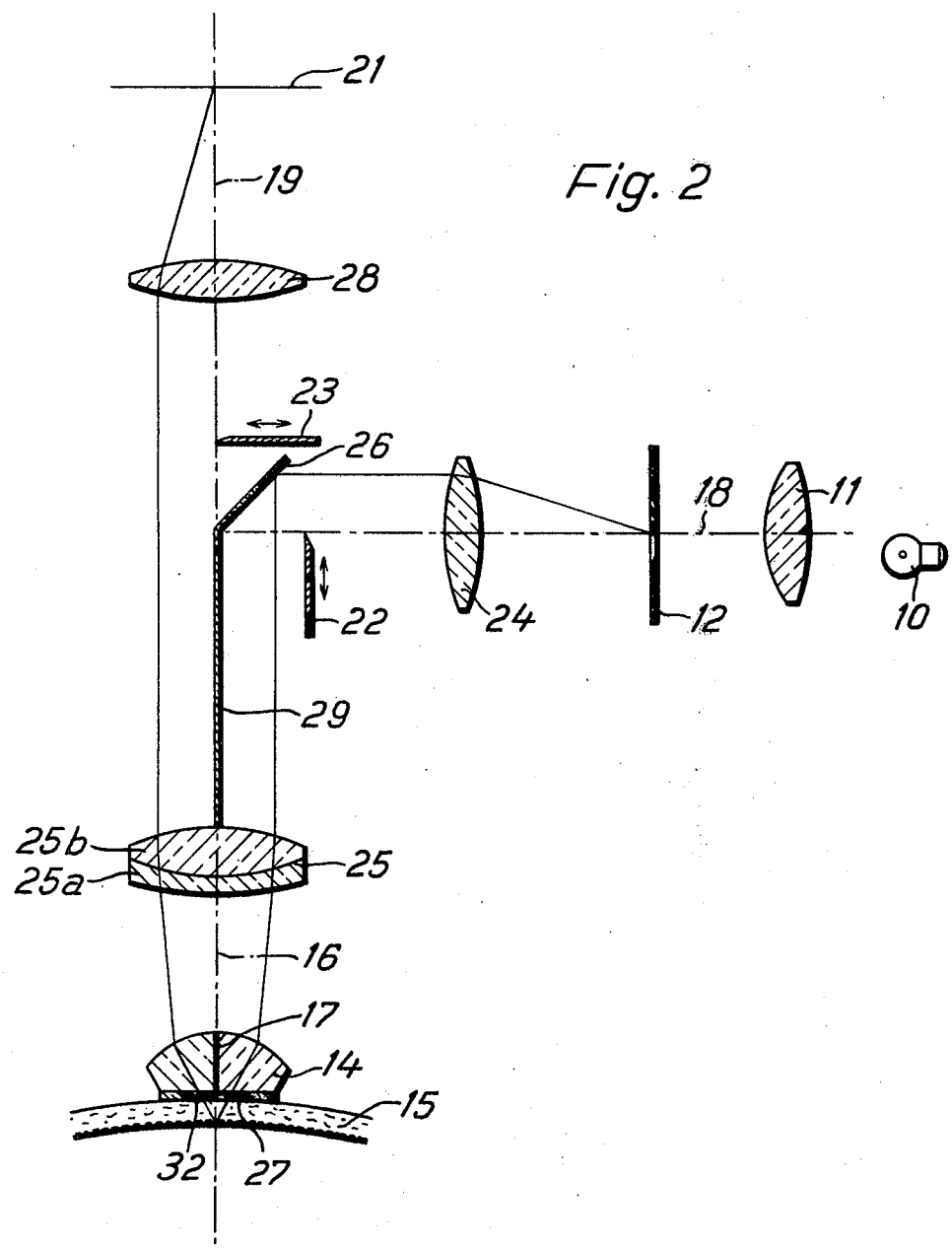
FIG. 2 is a side cross-sectional view showing an illuminating beam path reflected into the observation device by means of a mirror.

The arrangement shown in FIG. 2 represents the same imaging relationships as FIG. 1. However, the reflection by mirror 26 of the illuminating beam in the observation device results in a more compact structure. Here, because the beams are essentially parallel prior to reaching lens 14, the angle that the illuminating beam is incident on the object and the angle at which said object is observed, may be varied to a very limited extent only within the opening angle defined by the objective 25. Objective 25 comprising the lenses 25a and 25b serves to reducingly reproduce the luminous field diaphragm 12. Herein only one half of the objective 25 is used for the illuminating beam, i.e. the half receiving light reflected from deflecting mirror 26. The optical element 14 contains in this embodiment on its contact side toward the object 15 a cavity 27 to receive an immersion medium having a refractive index close to that of the object 15. The observation beam path passes through the left half of the optical element 14 and the objective 25. The lens 28 produces in the plane 21 an enlarged image of the object surface being examined.

The aperture diaphragms 22 and 23 are arranged and designed here so that upon insertion in the beam paths they affect only the rays passing near the optical axes 18 and 19. Thereby, the beam paths which are parallel to each other after their deflection by the mirror 26 may be further separated from each other and also the radiation cones may be separated from the cemented interface 17. Additionally, the two beam paths may be further separated at the mirror 26 geometrically by means of the diaphragm 29.

Figure 3:
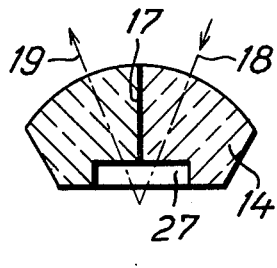
FIGS. 3–5 are side cross-sectional views showing various preferred embodiments of the optical element.
Figure 4:
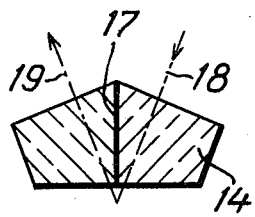
Figure 5:
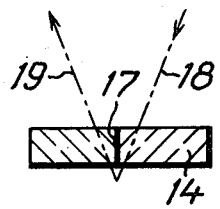
Figure 6:
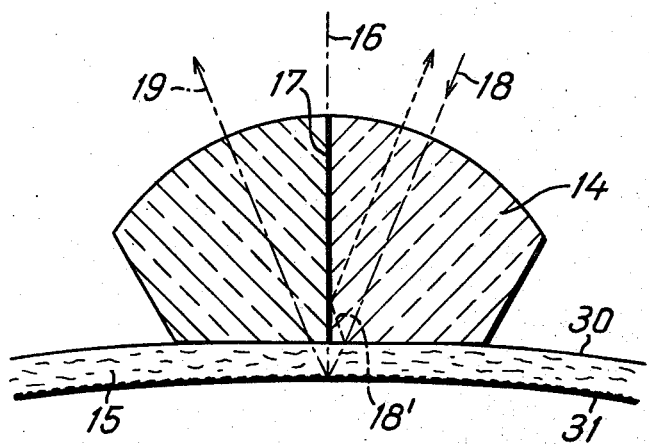
FIG. 6 is a side cross-sectional view showing the optical element in contact with a thin layer of tissue.
Figure 7:
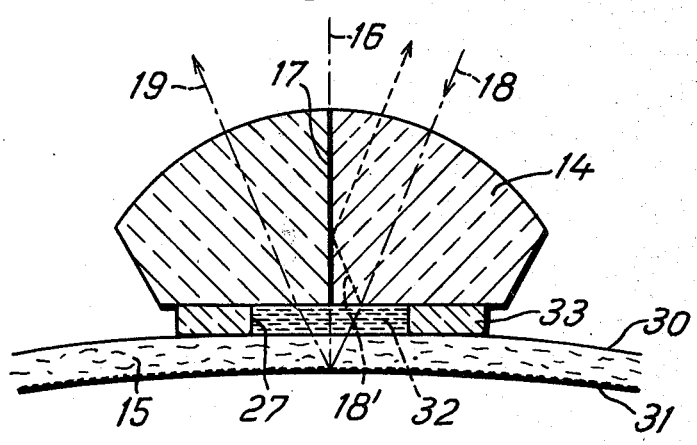
FIG. 7 is a side cross-sectional view of the optical element with an immersion medium in the area of examination.

FIG. 3 shows the optical element 14 as a planoconvex lens with a cavity 27 on the planar side in an individual representation. In FIG. 4 the optical element 14 is designed with sides facing both the illuminating and observation directions and has the form of a pentagonal prism. The inclination of the side surfaces is chosen so that the optical axes 18 and 19 are perpendicular to them. The optical element 14 shown in FIG. 5 is a parallel planar plate. FIGS. 6 to 8 are intended to visualize the operation of the optical element 14 during the suppression of reflections. For this purpose, in FIG. 6 an optical element 14 in direct contact with a front surface 30 of the object 15 is shown. A beam of light passing in the direction of the optical axis 18 is partially reflected at the interface between the optical element 14 and the front surface 30 of the object 15 due to the difference in refractive indices and the incident angle. A portion of light is passed through in the direction of an interior surface of object 15 such as rear surface 31. The rear surface 31 is desired to be examined. The reflection 18′ is, depending on the connecting opaque layer 17, either absorbed or reflected back in the direction of the illuminating beam path. Only the beams reflected from the rear surface 31 of the object enter the observation beam path 19.

In FIG. 7 an immersion medium 32 is inserted between the optical element 14 and the front surface 30 of the object. The cavity 27 necessary to hold the medium is formed by a ring 33 cemented on the planar surface of the optical element 14. The interface generating the interferring reflection is located between the optical element 14 and the immersion medium 32, because there is difference between refractive indices of the immersion medium and the optical element 14. If the refractive indices of the immersion medium and the surface 30 are close, there will be little or no interferring reflections caused by their interface.

The supporting action of the aperture diaphragms in the suppression of interferring reflections will be explained with the aid of the beam path shown in FIG. 8a in a simplified representation. The illumination beam limited by the aperture diaphragm 22 produces on the rear object surface 31 a reduced image of the luminous field 12. As has previously been noted, interferring reflections 18′ will be either reflected away from the observation beam path by connecting layer 17 or, if the connecting layer 17 is not large enough, blocked by diaphragm 23. By closing the aperture diaphragm 22, the corresponding light cone may be narrowed to the extent that all of the reflections are absorbed by the connecting layer 17. Alternatively or additionally, the aperture diaphragm 23 may be adjusted in the observation beam path so that none of the reflected beams passing far outside the optical axis 19 may be received by the optical device for observation.

Figure 8A:
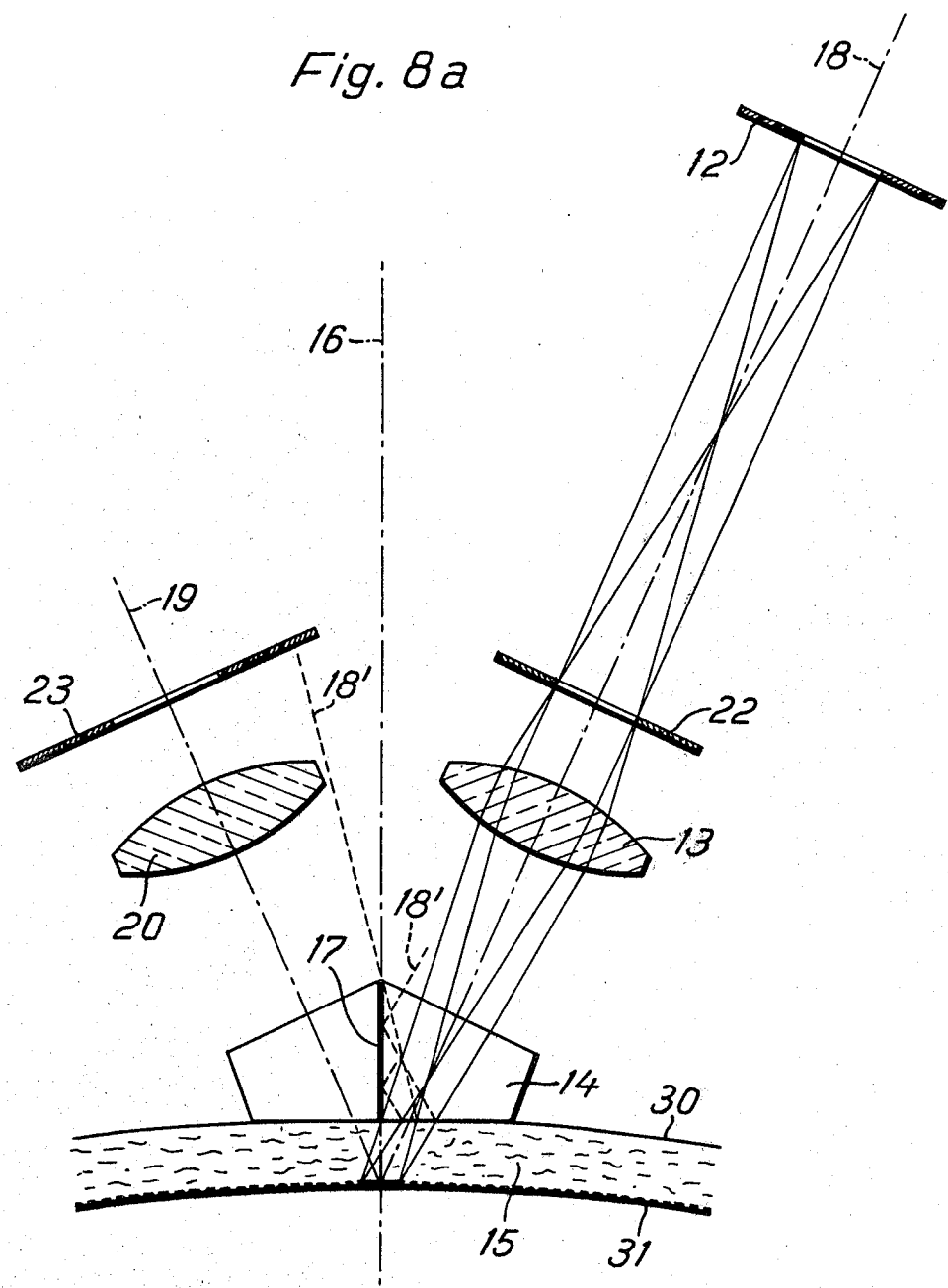
FIG. 8a is a side cross-sectional view of the present invention showing the illuminating and viewing beam paths.
Figure 8B:
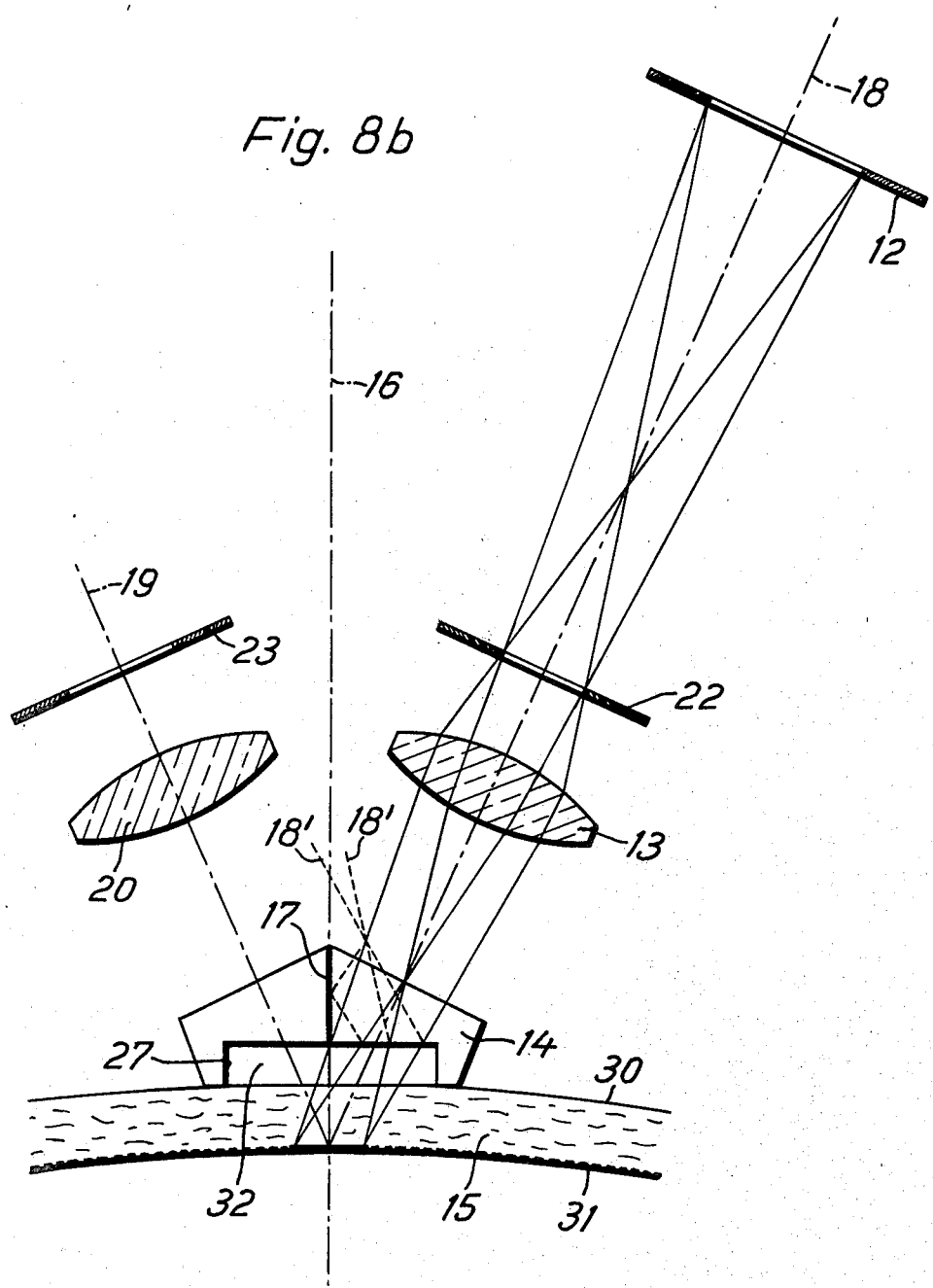
FIG. 8b is a side cross-sectional view of the present invention showing the beam paths with an immersion medium.

FIG. 8b is identical to FIG. 8a except that a cavity 27 filled with an immersion medium 32 is provided in the optical element 14. The result is a larger observable field on the rear surface 31 of object 15 may be illuminated. As long as medium 32 has a refractive index close to that of front surface 30 (cornea surface, for example), interferring reflections will not be produced therebetween. The interferring reflections 18′ created by the differences in refractive indices between medium 32 and optical element 14 will be cut off by connecting layer 17. By means of a suitable adjustment of the aperture diaphragms 22 and 23, here again the radiation cones for illumination and observation may be narrowed so that reflections not absorbed by the cemented surface 17 are not generated and thus are not received by the observation aperture.

The imaging beams represented in FIGS. 8a and 8b further illustrate the fact that the conditions of reflection at the interface between contact surface of the optical element 14 and the subject or medium surface are changed decisively, if the angle of the optical axes 18, 19 with respect to the normal to the surface 16 is altered. Even in the case of the optimum dimensioning of the reflection suppressing connecting layer 17, there may be boundary cases wherein the generation of interferring reflections must be prevented by varying the opening of the illumination cones by means of the diaphragms.

In cases where, between the front object surface 30 and the rear object surface 31, additional reflecting surfaces are present, reflections may pass the lower edge of the connecting layer 17 and arrive at the observation beam path. Suppression of these reflections may again be obtained by a suitable setting of the aperture diaphragm 22. These relationships may be derived from FIG. 8b, by presuming that the immersion medium 32 in the cavity 27 is absent. In this case, reflections would also appear on the front surface 30 of the object, and these reflections may be prevented from reaching the observation beam path by the unilateral cutting of the parts pointing toward the normal 16. Obviously, the aperture of the luminous field diaphragm 12 may also be reduced in a known manner. However, it is not necessary to narrow the opening as much as in known instruments.

Although the invention has been described relative to a number of specific embodiments, it is not so limited and many modifications and variations thereof will be readily apparent to those skilled in the art in light of the above teachings. It is, therefore, to be understood that, within the scope of the appended claims, the invention may be practiced otherwise than as specifically described.

What is claimed is:

1. An optical system for the reflecting microscopic examination of a rear surface of a biological tissue object, comprising:

imaging optical means for providing an illuminating beam having a path on a first axis;

viewing means for providing an observation beam having a path along a second axis;

lens means comprising:

a first lens portion positioned in said illuminating beam path for directing said illuminating beam to said object along a first direct lens path leading from an illuminating beam entry surface on the opposite side of said first lens portion from said object through a flat lens surface adjacent said object;

a second lens portion positioned in said observation beam path for directing reflected light from said rear surface of said object to said observation beam path along a second direct lens path leading from said flat lens surface adjacent said object through an observation beam exit surface on the opposite side of said second lens portion from said object;

said first and second lens paths forming an angle of not more than 90° therebetween in the region of said lens means; and said first and second lens portions having a light impermeable surface therebetween, said light impermeable surface being positioned in a plane bisecting the angle between the first and second axes, said light impermeable surface comprising means for preventing undesirable reflected and refracted light from said illuminating beam from entering said observation beam path and for permitting reflected light from said rear surface to enter said observation beam path to be examined;

said lens means including means for positioning said light impermeable surface along a normal to said object rear surface and perpendicular to the plane defined by said first and second axes.

2. An optical system in accordance with claim 1, wherein said illuminating beam entry surface and said observation beam exit surface comprise a curved surface and said lens means comprises the front lens of said imaging optical means and said viewing means.

3. An optical system in accordance with claim 1, wherein said first lens portion includes a surface which is perpendicular to said first axis and said second lens portion includes a surface perpendicular to said second axis and said lens means as a whole defines a pentagonal prism.

4. An optical system in accordance with any one of claims 1-3 wherein said system includes means defining a cavity between the flat surface of said lens means adjacent said object and the object, said optical system further including an immersion medium filling said cavity, said immersion medium having a refractive index compatible with said object.

5. An optical system in accordance with any one of claims 1-3, wherein there is further provided variable aperture diaphragm means inserted into at least one of said illumination and observation beam paths.

6. An optical system in accordance with claim 5, wherein said variable aperture diaphragm means includes diaphragms inserted into each beam path which are variable independent of each other.

7. An optical system in accordance with claim 5, wherein said variable aperture diaphragm means comprises a sliding diaphragm adumbrating at least one beam path.

* * * * *